US010932799B2

(12) United States Patent
Sirivong

(10) Patent No.: US 10,932,799 B2
(45) Date of Patent: Mar. 2, 2021

(54) EMBOLIC PROTECTION SYSTEM INCLUDING MULTIPLE FILTER BODIES

(71) Applicant: COVIDIEN LP, Mansfield, MN (US)

(72) Inventor: Sengkham Sirivong, Big Lake, MN (US)

(73) Assignee: Covidien LP, Mansfield, MA (US)

( * ) Notice: Subject to any disclaimer, the term of this patent is extended or adjusted under 35 U.S.C. 154(b) by 665 days.

(21) Appl. No.: 15/350,604

(22) Filed: Nov. 14, 2016

(65) Prior Publication Data
US 2018/0132873 A1 May 17, 2018

(51) Int. Cl.
A61B 17/221 (2006.01)
A61F 2/01 (2006.01)
(Continued)

(52) U.S. Cl.
CPC ............ A61B 17/221 (2013.01); A61F 2/013 (2013.01); A61F 2/95 (2013.01); A61B 2017/2212 (2013.01); A61B 2017/22062 (2013.01); A61B 2017/22081 (2013.01); A61F 2230/0067 (2013.01); A61F 2250/0018 (2013.01); A61F 2250/0039 (2013.01)

(58) Field of Classification Search
CPC ...... A61F 2/013; A61F 2/01; A61F 2002/018; A61F 2002/011; A61F 2002/016; A61F 2250/0098; A61F 2230/0067; A61F 2230/008; A61F 2230/0008; A61F 2230/0006; A61F 2230/001; A61M 2025/0183; A61M 2025/09183; A61B 17/12109; A61B 17/221; A61B 17/12022; A61B 17/12045; A61B 2017/2212; A61B 2090/3966; A61B 8/12; A61B 90/39
See application file for complete search history.

(56) References Cited
U.S. PATENT DOCUMENTS 7,993,363 B2 8/2011 Demond et al.
8,339,367 B2 12/2012 Dods
(Continued)

FOREIGN PATENT DOCUMENTS

DE 10049812 10/2000
WO 2006/076505 A2 7/2006
WO 2014/145469 A1 9/2014

OTHER PUBLICATIONS

PCT/US2017/060974, The International Search Report and the Written Opinion of the International Searching Authority, dated Feb. 2, 2018, 14pgs.

Primary Examiner — Mohamed G Gabr
(74) Attorney, Agent, or Firm — Shumaker & Sieffert, P.A.

(57) ABSTRACT

In some examples, an embolic protection system includes an elongated member, a first filter body mechanically connected to the elongated member and defining a first filter mouth and a first filter end, the first filter mouth being one of proximal or distal to the first filter end, and a second filter body mechanically connected to the elongated member and distal to the first filter body, the second filter body defining a second filter mouth and a second filter end, the second filter mouth being the one of proximal or distal to the second filter end. In some instances, at least a section of the elongated member between the first and second filter bodies may be flexible, and may be configured to conform to a shape of an arch between two vessels of a patient.

21 Claims, 7 Drawing Sheets

(51) Int. Cl.
    *A61F 2/95* (2013.01)
    *A61B 17/22* (2006.01)

(56) References Cited

U.S. PATENT DOCUMENTS

| | | |
|---|---|---|
| 8,486,105 B2 | 7/2013 | Demond et al. |
| 8,632,562 B2 | 1/2014 | Pal |
| 8,728,114 B2 | 5/2014 | Belson |
| 9,034,054 B2 | 5/2015 | Gerberding et al. |
| 9,211,178 B2 | 12/2015 | Rothstein et al. |
| 9,326,843 B2 | 5/2016 | Lee et al. |
| 2004/0116831 A1* | 6/2004 | Vrba ................. A61F 2/013 600/585 |
| 2006/0161241 A1* | 7/2006 | Barbut .............. A61F 2/013 623/1.15 |
| 2010/0004673 A1 | 1/2010 | Denison et al. |
| 2010/0268264 A1* | 10/2010 | Bonnette ........... A61B 17/221 606/200 |
| 2012/0172915 A1* | 7/2012 | Fifer ................. A61F 2/013 606/200 |
| 2013/0226223 A1 | 8/2013 | Spenser |
| 2014/0276922 A1* | 9/2014 | McLain ............. A61B 17/221 606/128 |
| 2015/0230910 A1 | 8/2015 | Lashinski |
| 2015/0335416 A1 | 11/2015 | Fifer et al. |
| 2016/0030153 A1 | 2/2016 | Galdonik et al. |
| 2016/0058541 A1 | 3/2016 | Schotzko et al. |
| 2016/0066880 A1* | 3/2016 | Stigall .............. A61B 8/0841 600/424 |
| 2016/0120636 A1 | 5/2016 | Gera et al. |

\* cited by examiner

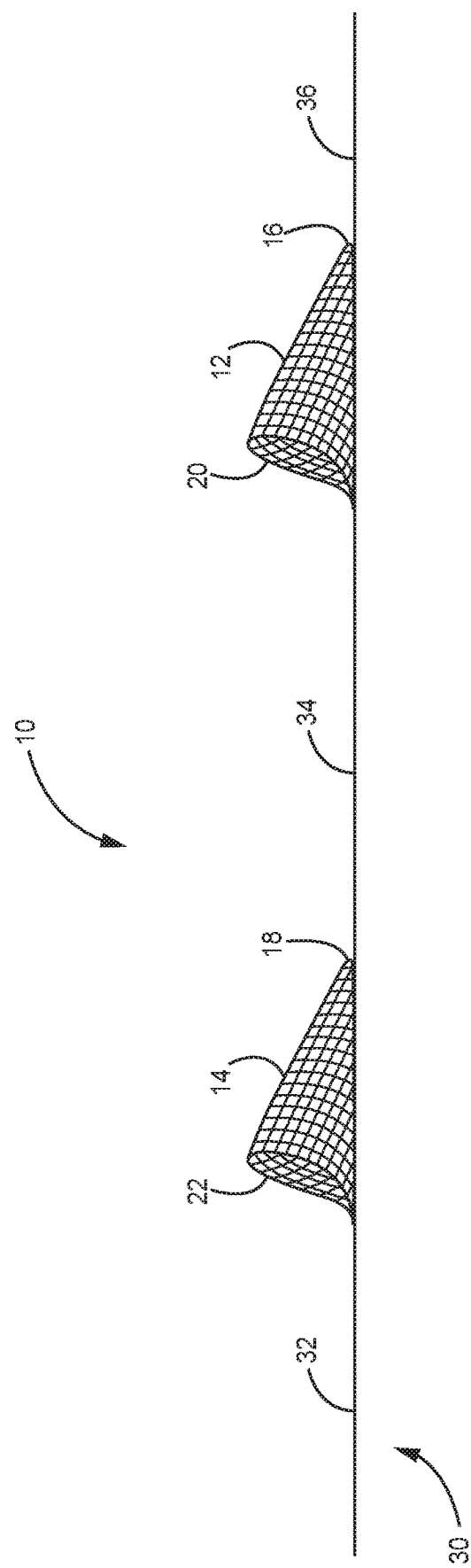

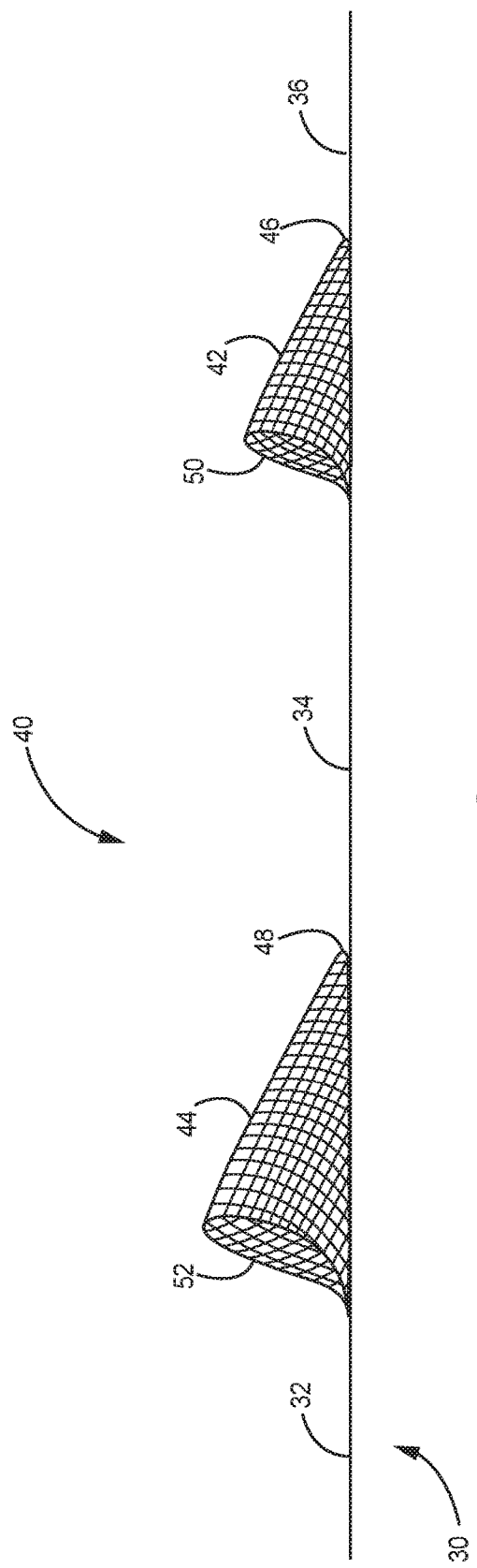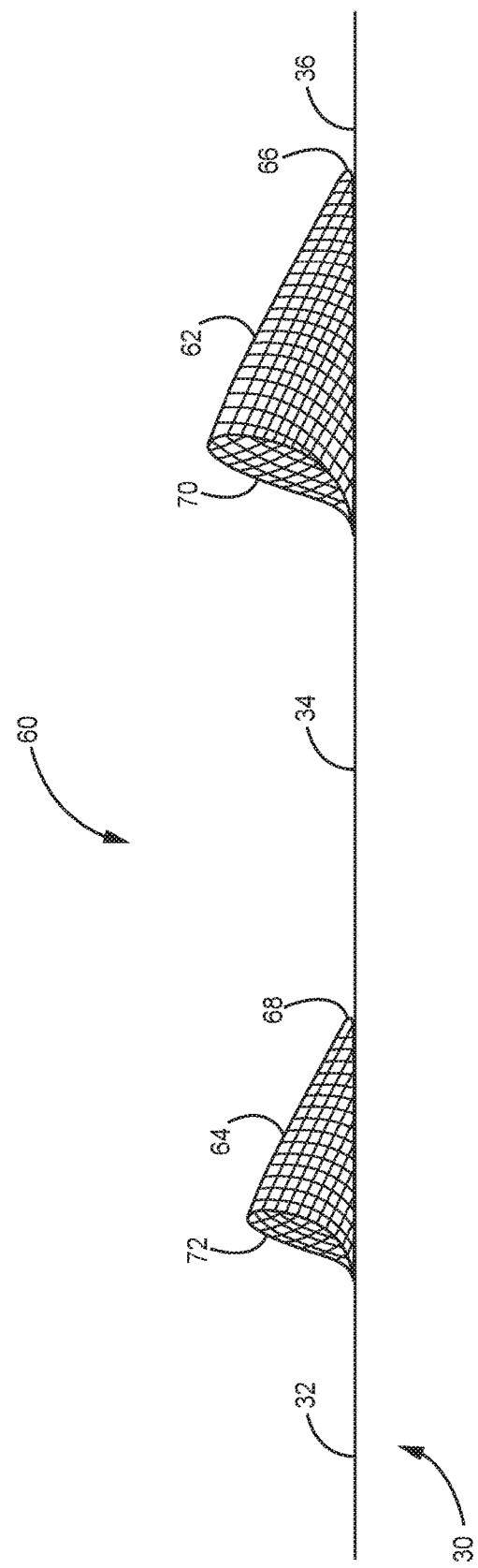

EMBOLIC PROTECTION SYSTEM INCLUDING MULTIPLE FILTER BODIES

TECHNICAL FIELD

The disclosure relates generally to embolic protection devices and systems.

BACKGROUND

Vessels may be treated to reduce or eliminate obstructions caused by arteriosclerotic disease. Interventional treatments can include the use of balloon angioplasty, stenting, thrombectomy, atherectomy, other procedures, or combinations thereof. During treatment, particulate debris can be generated at the treatment site. Infarcts, strokes, and other adverse events can be caused when debris embolizes into vasculature from the treatment site.

To help reduce or prevent embolization of debris, embolic protection devices have been developed. During a treatment procedure, such devices can be deployed distal or proximal to the treatment site. Embolic protection devices can remove emboli from the bloodstream by filtering debris from the blood or by occluding blood flow followed by aspiration of debris.

SUMMARY

This disclosure describes example embolic protection systems, which can be used to, for example, capture debris (e.g., plaque, blood clots or the like) during a vascular procedure. The embolic protection systems include at least two filter bodies configured to capture particulate debris. The at least two filter bodies are mechanically connected to an elongated member, and include filter mouths that face in the proximal or distal direction. A section of the elongated member between the first and second filter bodies is flexible, e.g., more flexible than a proximal section of the elongated member proximal to the proximal-most filter body. Also described herein are techniques directed to introducing, using, and retrieving the embolic protection system.

Clause 1: In some examples, a system comprises an elongated member; a first filter body mechanically connected to the elongated member and defining a first filter mouth and a first filter end, the first filter mouth being one of proximal or distal to the first filter end; and a second filter body mechanically connected to the elongated member distal to the first filter body, the second filter body defining a second filter mouth and a second filter end, the second filter mouth being the one of proximal or distal to the second filter end, wherein at least a section of the elongated member between the first and second filter bodies is flexible.

Clause 2: In some of the examples of the system of clause 1, the first and second filter bodies are a same size.

Clause 3: In some of the examples of the system of clause 1, the first and second filter bodies are different sizes.

Clause 4: In some of the examples of the system of any of clauses 1-3, the first filter mouth and the second filter mouth are a same size.

Clause 5: In some of the examples of the system of any of clauses 1-3, the first filter mouth and the second filter mouth are different sizes.

Clause 6: In some of the examples of the system of any of clauses 1-5, the first and second filter mouths are proximal to the first and second filter ends, respectively.

Clause 7: In some of the examples of the system of any of clauses 1-6, the first and second filter mouths are distal to the first and second filter ends, respectively.

Clause 8: In some of the examples of the system of any of clauses 1-7, a proximal section of the elongated member proximal to the first filter body is more stiff than the section of the elongated member between the first and second filter bodies.

Clause 9: In some of the examples of the system of any of clauses 1-8, the proximal section of the elongated member proximal to the first filter body is self-supporting.

Clause 10: In some of the examples of the system of any of clauses 1-9, the section of the elongated member between the first and second filter bodies is configured to substantially conform to a shape of an arch between two vessels of a patient.

Clause 11: In some examples, a system comprises an elongated member; a first filter body mechanically connected to the elongated member and defining a first filter mouth and a first filter end, the first filter mouth being one of proximal or distal to the first filter end; and a second filter body mechanically connected to the elongated member distal to the first filter body, the second filter body defining a second filter mouth and a second filter end, the second filter mouth being the one of proximal or distal to the second filter end, wherein the elongated member comprises a proximal section proximal to the first and second filter bodies and an intermediate section between the first and second filter bodies, the intermediate section being more flexible than the proximal section.

Clause 12: In some of the examples of the system of clause 11, the first and second filter bodies are a same size.

Clause 13: In some of the examples of the system of clause 11, the first and second filter bodies are different sizes.

Clause 14: In some of the examples of the system of any of clauses 11-13, the first filter mouth and the second filter mouth are a same size.

Clause 15: In some of the examples of the system of any of clauses 11-13, the first filter mouth and the second filter mouth are different sizes.

Clause 16: In some of the examples of the system of any of clauses 11-15, the proximal section of the elongated member is self-supporting.

Clause 17: In some examples, a method comprises introducing an embolic protection system into a vasculature of a patient, the embolic protection system comprising an elongated member; a first filter body mechanically connected to the elongated member and defining a first filter mouth and a first filter end, the first filter mouth being one of proximal or distal to the first filter end; and a second filter body mechanically connected to the elongated member distal to the first filter body, the second filter body defining a second filter mouth and a second filter end, the second filter mouth being the one of proximal or distal to the second filter end, wherein at least a section of the elongated member between the first and second filter bodies is flexible; positioning the first filter body in a first vessel; and positioning the second filter body in a second vessel.

Clause 18: In some examples of the method of clause 17, the first and second vessels are branches of a main vessel.

Clause 19: In some examples of the method of clause 17 or 18, introducing the embolic protection system into the vasculature of the patient comprises introducing a delivery catheter into the vasculature, the embolic protection system being positioned within an inner lumen of the delivery catheter.

Clause 20: In some examples, the method of any of clauses 17-19 further comprises, after positioning the first and second filter bodies in the first and second vessels, respectively, removing plaque at a treatment site in the vasculature of the patient, the first and second vessels being downstream of the treatment site.

Clause 21: In some examples, the method of any of clauses 17-20 further comprises, after positioning the first and second filter bodies in the first and second vessels, respectively, inflating a balloon at a treatment site in the vasculature, the first and second vessels being downstream of the treatment site.

Clause 22: In some examples, the method of any of clauses 17-21 further comprises, after positioning the first and second filter bodies in the first and second vessels, respectively, positioning a stent at a treatment site in the vasculature, the first and second vessels being downstream of the treatment site.

The details of one or more examples are set forth in the accompanying drawings and the description below. Other features, objects, and advantages of examples according to this disclosure will be apparent from the description and drawings, and from the claims.

BRIEF DESCRIPTION OF DRAWINGS

FIG. 1 is a side view of an example embolic protection system including a first filter body and a second filter body, each of which are mechanically connected to an elongated member.

FIG. 2A is a side view of another example embolic protection system including a first filter body and a second filter body, each of which are mechanically connected to an elongated member, where the first and second filter bodies are different sizes.

FIG. 2B is a side view of another example embolic protection system including a first filter body and a second filter body, each of which are mechanically connected to an elongated member, where the first and second filter bodies are different sizes.

DETAILED DESCRIPTION

Figure 3A:
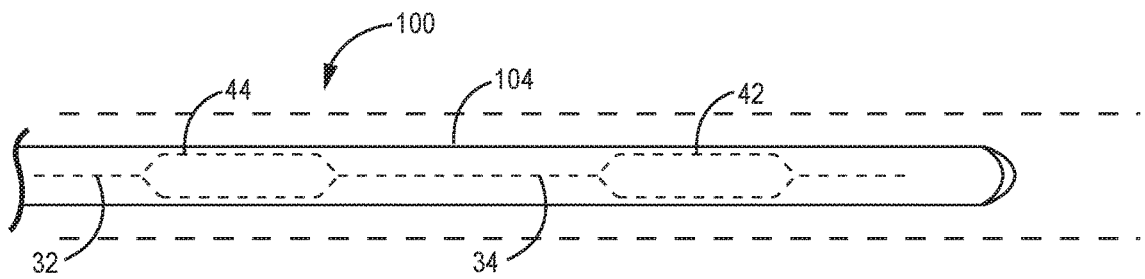
FIG. 3A is a side view of the system of FIG. 2A being introduced into a blood vessel (shown in cross-section) with the aid of a delivery catheter.

An embolic protection system can be used to, for example, capture debris (e.g., plaque, blood clots or the like) during a vascular procedure, such as a vascular surgery or endovascular treatment of vessels, including, but not limited to, thrombectomy, atherectomy, balloon angioplasty, stent deployment, or other procedures used to reduce or eliminate obstructions in the vasculature. Example embolic protection systems described herein include at least two filter bodies configured to capture the debris in a blood stream of a patient, which may help debris generated by the vascular procedure from passing into one or more downstream locations in the vasculature.

The shape, length, and other characteristics of an embolic protection device may be designed based on anatomical characteristics in the vicinity of a treatment site within a patient. Some anatomical characteristics may present design challenges due to their shape or configuration. For example, some design challenges may arise when configuring an embolic protection system to be used in a vessel that diverges into more than one vessel at a location downstream of an obstruction. As an example, an obstruction may exist in the aorta, which diverges at the aortic arch into downstream arteries that supply the brain, including the brachiocephalic artery and the left common carotid artery. If an interventional treatment is performed to reduce or eliminate such an obstruction without deploying embolic protection devices at the downstream vessels, then particulate debris generated at the treatment site can enter an unprotected artery leading to the brain. Some embolic protection devices that operate by occluding or reversing blood flow may not be suitable for placement in arteries that lead to the brain, e.g., because of the adverse effects that can arise from the deprivation of blood to the brain. Thus, it may be advantageous in some cases to protect arteries leading to the brain from particulate debris while simultaneously maintaining blood flow therethrough during an upstream treatment procedure, such as by utilizing filter devices through which blood can pass but particulate debris cannot.

This disclosure describes example embolic protection systems that can be used to capture particles in multiple vessels of a patient. Example embolic protection systems described comprise at least two filter bodies connected to an elongated member. While embolic protection systems that includes two filter bodies connected to an elongated member are primarily described herein, in other examples, embolic protection systems can include more than two filter bodies.

In some examples, a first filter body and a second filter body are mechanically connected to an elongated member and may be configured to capture particles present in the bloodstream of a patient, e.g., while allowing blood to flow through the filter bodies such that the material of the filter bodies does not occlude blood flow. At least a section of the elongated member positioned between the first filter body and the second filter body is flexible, which may allow the section to substantially conform (e.g., conform or nearly conform) to a shape of an arch between two vessels of a patient. The arch can be, for example, a vessel wall that extends between two vessels (e.g., branches). For example, to traverse between one vessel to another vessel, the elongated member may extend along the arch.

For example, a distal section of the elongated member distal to the first and second filter bodies and an intermediate section of the elongated member extending between the first and second filter bodies may be relatively flexible, e.g., compared to a proximal section of the elongated member, proximal to the filter bodies. As another example, the intermediate section of the elongated member extending between the first and second filter bodies may be more flexible than a proximal section of the elongated member proximal to both the first and second filter bodies and/or the distal section of the elongated member. For example, the proximal section may be relatively stiff (e.g., self-supporting) to allow the embolic protection system to be pushed in a distal direction by a force applied to the proximal section and/or rotated by a torsional force applied to the proximal section. That is, the proximal section may have sufficient columnar strength to allow the first and second filter bodies to be pushed distally in a body lumen by a pushing force applied to the proximal section (including the proximal end) of the elongated member, and/or may be sufficiently stiff to allow the first and second filter bodies to be rotated in a body lumen by a rotational force applied to the proximal section of the elongated member. For example, in some examples, the proximal section of the elongated member may be similar in construction to a guidewire, although other constructions are possible in other examples.

In some example techniques, the first filter body may be positioned within a first blood vessel (or other body lumen) of a patient, and the second filter body may be positioned within a second blood vessel (or other body lumen) of the patient. With the first filter body and second filter body so positioned, a procedure to reduce or eliminate an occlusion, or otherwise treat the vessel from a third vessel may be performed. In some examples, the first, second, and third blood vessels may be part of a common blood vessel. For example, the "third" blood vessel may be a main blood vessel, the "first" blood vessel may be a branch of the main blood vessel, and the "second" vessel may be a second branch of the main blood vessel or a part of the main blood vessel downstream of the opening to the second blood vessel. The first filter body and the second filter body may be configured to capture particles resulting from the disruption of the occlusion, thereby helping to minimize or even prevent the particles from traveling further down the first vessel and the second vessel, respectively.

While blood vessels are primarily referred to herein, the embolic protection systems and techniques described herein can be used with other body lumens of a patient. The filter bodies of the embolic protection system may be used to capture particles in other body lumens.

FIG. 1 is a side view of an example embolic protection system 10, which is configured to help minimize or prevent the embolization of particles in the vasculature of a patient following a treatment procedure to reduce or eliminate an occlusion, or to otherwise treat a vessel. System 10 can be used with any suitable treatment procedure. In some examples, a treatment procedure may include treatment of an atherosclerotic plaque in a body vessel by cutting, abrading, or otherwise disrupting the plaque with an atherectomy device. In other examples, the treatment procedure may include treatment of an atherosclerotic plaque with an expandable balloon device configured to compress, fracture, or otherwise disrupt the plaque. In other examples, the treatment procedure may further include stenting or otherwise reinforcing a portion of a body vessel at a treatment site.

In the illustrated example, embolic protection system 10 includes elongated member 30, first filter body 12, and second filter body 14. First filter body and second filter body 12, 14 are mechanically connected to elongated member 30, with first filter body 12 being positioned distal to second filter body 14. The components of embolic protection system 10 are made from biocompatible materials.

Elongated member 30 mechanically couples filter bodies 12, 14 together, and helps deploy filter bodies 12, 14 in vasculature (or another body lumen) of a patient, as well as retrieve filter bodies 12, 14 from the vasculature. In some examples, elongated member 30 can function as a guide structure for filter bodies 12, 14, as elongated member 30 facilitates deployment and retrieval of filter bodies 12, 14 in a patient, as described below. First and second filter bodies 12, 14 may be mechanically coupled to elongated member 30 using any suitable technique. In some examples, first and second filter bodies 12, 14 may be coupled to elongated member 30 by adhesives, solder, welding, crimped elements such as bands or beads, and other suitable fixation mechanisms and/or elements. In other examples, filter bodies 12, 14 may be formed directly onto elongated member 30, such as by incorporating one or more sections of elongated member 30 into a material forming filter bodies 12, 14.

In some examples, filter bodies 12, 14 are fixed relative to elongated member 30. For example, one or both of the proximal and distal ends of each of filter bodies 12, 14 may be affixed to elongated member 30, such as by welding, adhesive, a mechanical connection, e.g., crimping a part of the respective filter body to elongated member 30. In some examples, system 10 may include annular rings or other fixed elements to which the material of filter bodies 12, 14 may be secured. The fixed elements may include an element that is crimped, adhered, soldered, or otherwise fastened directly to the elongated member 30. In other examples, filter bodies 12, 14 may be attached directly to elongated member 30.

In other examples, filter bodies 12, 14 may be movable (e.g., axially slidable) relative to elongated member 30. For example, filter bodies 12, 14 may be connected to elongated member 30 using rings or the like that may slide along elongated body 30. In some examples in which filter bodies 12, 14 are movable relative to elongated body 30, elongated body 30 may include mechanical stops that limit the relative proximal and distal sliding of filter bodies 12, 14 along the longitudinal axis of elongated member 30. The ability of filter bodies 12, 14 to slide relative to elongated member 30 may provide numerous one or more benefits. For example, the slidability of filter bodies 12, 14 relative to elongated member 30 may allow a clinician to adjust the distance between filter body 12 and filter body 14, during any of the deployment, placement, and retrieval of filter bodies 12, 14, e.g., to accommodate different target tissue sites within a patient.

In some examples, the slidability of filter bodies 12, 14 may help a clinician more predictably place filter bodies 12, 14 at target deployment sites within vasculature of a patient. For example, a clinician may determine, during filter placement, that a distance between two target deployment sites for filter bodies 12, 14 is less than anticipated. In such an example, the clinician may slide one or both of filter bodies 12, 14 relative to elongated body 30 so as to decrease the distance between filter bodies 12, 14, thereby aiding in the placement and/or retrieval of filter bodies 12, 14. As another illustration, a clinician may determine, during filter placement in vasculature of a patient, that a distance between two target deployment sites is greater than anticipated. In this example, the clinician may slide one or both of filter bodies 12, 14 relative to elongated member 30 so as to increase the distance between filter bodies 12, 14, thereby aiding in the placement and/or retrieval of filter bodies 12, 14.

In other examples, the slidability of filter bodies 12, 14 may be beneficial during a retrieval of filter bodies 12, 14 that may be undertaken during or after a treatment procedure. For example, it may be desirable to decrease the distance between filter bodies 12, 14 in order to reduce the possibility that one or both of filter bodies 12,14 may become oriented in a manner that would allow trapped particles to escape from the filter body. In this example, a decreased distance between filter bodies 12, 14 may permit a greater amount of proximal pulling force to be transferred from elongated member 30 to first filter body 12 during retrieval, which may in turn help to keep first filter body 12 aligned substantially parallel with elongated member 30 with filter mouth 20 facing in a proximal direction.

Elongated member 30 includes at least two sections, including proximal section 32 and intermediate section 34. In some examples, elongated member 30 is formed as a unitary body extending from a proximal end of system 10 to a distal end of system 10, such that sections 32, 34 are continuous. In other examples, elongated member 30 may be formed as a number of discontinuous sections interrupted by filter bodies 12, 14.

Regardless of whether elongated member 30 is formed as a unitary body or includes a number of discontinuous sections, proximal section 32 may be situated proximal to second filter mouth 22, and intermediate section 34 extends between filter bodies 12, 14. For example, intermediate section 34 may extend from first filter end 16 to second filter mouth 22, as illustrated in FIG. 1. Thus, a length of intermediate section 34 may be substantially equal (e.g., equal or within a few millimeters) to the length between first filter end 16 and second filter mouth 22 measured a long a longitudinal axis of elongated member 30. In other examples, proximal section 32 may be situated proximal to second filter end 18, and intermediate section 34 may extend from first filter end 16 to second filter end 18. Thus, a length of intermediate section 34 may be substantially equal to the length between first filter end 16 and second filter end 18 measured a long a longitudinal axis of elongated member 30. In other examples, intermediate section 34 may extend somewhere between first filter end 16 to second filter mouth 22, but is of sufficient length to impart relative movement between filter bodies 12, 14, as discussed below.

In the example illustrated in FIG. 1, elongated member 30 further comprises distal section 36, which may be situated distal to first filter end 16. However, in other examples, elongated member 30 may not extend distally past first filter body 12, e.g., may terminate at the mouth 20 or end 16 of filter body 12.

Elongated member 30 is sufficiently flexible to allow system 10 to be navigated through the vasculature, which may be relatively tortuous in some cases, without kinking or becoming arrested by the vasculature en route to the deployment site for filter bodies 12, 14. In some examples, at least some sections of elongated member 30 may comprise an elongated metal wire, although other materials, such as polymers, can also be used in other examples in addition to or instead of the metal wire. Suitable materials for one or more sections of elongated member 30 include, but are not limited to, nitinol (nickel titanium), stainless steel, cobalt-chromium-nickel molybdenum-iron alloy (commercially available under the trade designation Elgiloy™), carbon fiber and its composites, and engineered polymers such as liquid crystal polymers, polyether ether ketone (PEEK), polyimide, polyester, and the like. Elongated member 30 may be solid, in some examples, or may be hollow over some or all of its length.

Sections 32, 34, and 36 of elongated member 30 may be made from the same material, or may be made from different materials than one another. Further, in some examples, regardless of whether sections 32, 34, 36 are formed from the same or different materials, two or more of the sections 32, 34, 36 may have different physical properties. For example, intermediate section 34 may be more flexible than proximal section 32 and, in some cases, more flexible than distal section 36. This may allow filter bodies 12, 14 to be moved (e.g., six degrees of relative movement) relative to each other. As discussed below, in some examples, intermediate section 34 has sufficient flexibility to substantially conform (e.g., follow or nearly follow the curvature of) to an arch, branch, or similar structure in the vasculature of a patient, such as between two vessels within the vasculature of a patient.

The flexibility and length of intermediate section 34 may be selected to configure system 10 to provide embolic protection to multiple vessels. Moreover, the provision of a single elongated member having more than one filter body may provide the benefits of easier introduction to the vasculature, reduced likelihood of kinking or tangling, and easier post-procedure retrieval, among others. In some examples, such benefits may be provided by a configuration of intermediate section 34 that is different than the configuration of sections 32, 36. The different configuration can be achieved by, for example, one or more of a different geometry (e.g., in cross-section or the shape the section defines), a different size, a different material, a different surface attributes (e.g., cut-outs), or any combination thereof.

For example, at least a part or the entire intermediate section 34 may define a predetermined three-dimensional configuration, such as a coiled shape, when not subjected to a longitudinal pulling force (along a longitudinal axis of elongated member 30) applied to a proximal end of system 10. In another example, a material of intermediate section 34 may be formed so as to have a folded shape, such as accordion-folded or a fan-folded, when not subjected to a longitudinal pulling force applied to a proximal end of system 10. In these examples, intermediate section 34 may assume a longitudinally compressed configuration when not subjected to a pulling force, thereby maintaining intermediate section 34 in a configuration associated with a reduced likelihood of kinking or tangling until intermediate section 34 is subjected to a pulling force during deployment or retrieval of system 10. In addition, the predetermined three-dimensional configuration of intermediate section 34 may also increase the flexibility of intermediate section 34, e.g., may allow intermediate section 34 to effectively increase in length, which may further facilitate the implantation of system 10 in vasculature of a patient.

In some examples in which intermediate section 34 defines a predetermined three-dimensional configuration when not subjected to a longitudinal pulling force applied to a proximal end of system 10, intermediate section 34 may be formed form a shape memory material or a superelastic material, such as nitinol, although other materials may also be used in other examples.

In some examples, at least a part or the entire proximal 32 and/or distal section 36 may also define a predetermined three-dimensional configuration, such as a coiled shape, when not subjected to a longitudinal pulling force applied to a proximal end of system 10. In these examples, sections 32, 36 may have the same predetermined three-dimensional configuration as intermediate section 34, or may have a different three-dimensional configuration.

The different flexibility of the sections 32, 34, 36 can be achieved using any suitable technique or combination of techniques, such as by the materials from which the sections 32, 34, 36 are formed, the cross-sectional shape, the cross-sectional dimension (e.g., diameter in the case of circular cross-sections), and the presence or absence of structural support members, as described below. For example, different flexibilities of sections 32, 34, 36 may be achieved by forming the sections 32, 34, 36 from different materials, such as two or more of the materials described above with respect to elongated member 30, where the materials may have different properties. In these examples, sections 32, 34, 36 may have substantially the same cross-sectional dimensions, e.g., diameters, or may have substantially different cross-sectional dimensions. In addition to or instead of the materials, the different flexibility of the sections 32, 34, 36 may be achieved by selecting the configuration (e.g., geometry) of the material to achieve the desired flexibility. For example, proximal section 32 may be formed from a wire having a greater thickness than the wire forming intermediate section 34, such that intermediate section 34 is more flexible than proximal section 32.

In addition to or instead of the examples described above, the different flexibility of the sections 32, 34, 36 may be achieved by adding one or more structural support members (not shown) to elongated member 30. In this example, any of sections 32, 24, 36 may optionally include one or more structural support members. Such structural support members may, in some examples, include a metal or polymer filament, coil, or strut that may be braided, woven, or otherwise attached to a material of any of sections 32, 34, 36. Structural support members may provide structural support (e.g., increasing the columnar strength or torqueability) to any of sections 32, 34, 36 during deployment, use, and retrieval of system 10, thereby helping a clinician to maneuver system 10 within the vasculature of a patient and ensure proper placement of system 10. In some examples, a structural support member may extend longitudinally along part of a length of any of sections 32, 34, 36. In other examples, a structural support member may extend longitudinally along all of a length of any of sections 32, 34, 36.

In some examples, at least a portion of proximal section 32 may have sufficient stiffness to be self-supporting, whereas intermediate section 34 may not have sufficient stiffness to be self-supporting. In some examples, the self-supporting stiffness of proximal section 32 may be sufficient to provide pushability and torqueability to proximal section 32. Thus, a pushing or torqueing (rotational) force applied to proximal section 32, either directly or through a handle or other attachment at a proximal section 32, may be translated into the advancement or rotation, respectively, of elongated member 30 through the vasculature of a patient. A pushability feature of proximal section 32 may be similar to the pushability provided by a guidewire of a medical device, such that the pushability allows a clinician to navigate filter bodies 12, 14 to a deployment site within the vasculature of the patient. In some examples, proximal section 32 may itself comprise a guidewire.

In some examples, a distal-most part of proximal section 32 may be relatively more flexible than a proximal-most part of proximal section 32. For example, the distal-most part may have the same or nearly the same flexibility as intermediate section 34. In these examples, the stiffer part of proximal section 32 may be configured to engage with a part of filter 14, to allow the stiffer part of proximal section 32 may apply a pushing force to filter 14, e.g., to place filter 14 or filter 12 at a target site within a patient. In these examples, the more flexible distal-most part of section 32 may be folded or otherwise moved out of the way, such that the stiffer part of proximal section 32 may directly engage with filter 14. As an example, a proximal side of filter 14 may define a recess configured to receive the distal tip of the stiffer part of proximal section 32. The relatively more flexible section of proximal section may allow there to be some slack between the stiffer part of proximal section 32 and filter 14, such that movement of the stiffer part of proximal section 32 does not necessarily cause movement of filter 14.

Intermediate section 34, which may not have sufficient stiffness to be self-supporting, may allow intermediate section 34 to flexibly traverse an arch or other anatomical feature separating more than one branch of a vessel within the vasculature of the patient. For example, intermediate section 34 may have sufficient flexibility to allow first filter body 12 to be deployed within a first branch of a main vessel, and for second filter body 14 subsequently to be deployed in a second branch of the main vessel without dislodging first filter body 12 from its deployed position within the first branch.

In some examples in which elongated member 30 includes distal section 36, distal section 36 of elongated member 30 may have any suitable configuration. For example, distal section 36 may comprise a floppy tip, which may provide an atraumatic and radiopaque terminus for elongated member 30 to facilitate initial placement or subsequent advancement of system 10 through vasculature, and may help a clinician verify suitable tip placement via fluoroscopic imaging. In some examples, distal section 36 may comprise a springy or resilient material, including those identified above. In addition, in some examples, the material of distal section 36 may be radiopaque or made radiopaque by plating, or by using core wires, tracer wires, beads, or fillers that have good X-ray absorption characteristics compared to the human body. In some examples, distal section 36 may be made of the same material as at least one of proximal section 32 and intermediate section 34. In other examples, distal section 36 may be made from a different material than either of proximal section 32 and intermediate section 34.

Filter bodies 12, 14 are configured to filter particles from a body lumen of a patient. For example, in some examples, filter bodies 12, 14 are configured to filter emboli from blood flowing through a blood vessel of a patient. Filter bodies 12, 14 have any suitable configuration for filtering particles, such as, but not limited, to a braided structure, knitted structure, woven structure, or non-woven structure. Filter bodies 12, 14 may be formed from any number of suitable materials, some of which may have self-expanding properties. Suitable materials include, but are not limited to, metals such as titanium and its alloys (such as nitinol), stainless steel, cobalt-chromium-nickel-molybdenum-iron alloy (commercially available under the trade designation Elgiloy™), carbon fiber and its composites, and engineered polymers such as liquid crystal polymers, polyetheretherketone (PEEK), polyimide, polyester, silk, and the like.

In some examples, filter bodies 12, 14 may optionally include one or more filter support structures. Such filter support structures may, in some examples, include a metal or polymer filament or strut that may be braided, woven, or otherwise attached to a material of filter bodies 12, 14. Filter support structures may provide structural support to filter bodies 12, 14 upon filter deployment, thereby helping filter bodies 12, 14 to maintain an expanded state within the vasculature of a patient. In some examples, a filter support structure may extend longitudinally along a filter body from the filter end to the filter mouth. In other examples, a filter support structure may extend around a circumference or perimeter of a filter mouth. Filter support structures, as well other elements of filter bodies 12, 14, may be self-expanding. A shape memory or superelastic metal, such as nitinol, is particularly suitable for those applications in which it is desired for an element, such as a filter body 12, 14, a filter mouth 20, 22, or a support structure thereof, to assume a pre-determined three-dimensional shape upon deployment in vasculature of a patient. For example, nitinol tubular braid can be heat set into a desired shape of a filter body, compressed for delivery to a deployment site, and then released to resume the heat-set shape.

First filter body 12 defines a first filter mouth 20 and first filter end 16, and second filter body 14 defines second filter mouth 22 and second filter end 18. Filter mouths 20, 22 define the openings through which particles may be captured in the respective filter bodies 12, 14. Filter mouths 20, 22 can have any suitable size, which may depend on the application for embolic protection system 10. For example, in some examples, first filter mouth 20 and second filter mouth 22 may each have a diameter of approximately 5.50-7.50 mm, which may be suitable for deployment into the right and left common carotid arteries of an adult human patient having a relatively large body size. In another example, first filter mouth 20 and second filter mouth 22 may each have a diameter of approximately 5.30-7.00 mm, which may be suitable for deployment into the right and left common carotid arteries of an adult human patient having a relatively small body size.

In the example shown in FIG. 1, first filter mouth 20 and second filter mouth 22 have substantially the same dimensions. For example, first filter mouth 20 and second filter mouth 22 may have substantially the same diameter, circumference, or perimeter size (for non-circular filter mouths). However, in other examples, filter mouths 20, 22 may have different dimensions. For example, filter mouth 20 may have a larger diameter, circumference, or perimeter size than a corresponding dimension of filter mouth 22. In other examples, filter mouth 20 may have a smaller diameter, circumference, or perimeter than a corresponding dimension of filter mouth 22. The dimensions of filter mouths 20, 22 may depend on dimensions or other aspects of the vasculature in which filter bodies 12, 14, respectively, are deployed.

The ability to configure system to have filter bodies with different sized mouths 20, 22 may allow system 10 to be configured to deployed to different portions of the vasculature. For example, first filter mouth 20 and second filter mouth 22 may each have a diameter of approximately 4.25 mm-6.00 mm and 3.75-5.50 mm, respectively, which may be suitable for deployment of system 10 into the right and left internal carotid arteries of differently-sized patients.

The maximum outer dimension, such as a maximum outer circumference or a maximum outer perimeter, of at least one a mouth of a filter or the filter body, when deployed, may be selected to substantially span the lumen of the vessel into which it is to be introduced, in order to minimize the number of particles flowing past the filter body 12, 14. The example diameters described herein for first filter mouth 20 and second filter mouth 22 are not exhaustive. Filter mouths having any suitable diameter may be employed, and may be sized for deployment into the vasculature of a human child, another mammalian animal, or a non-mammalian animal.

Filter bodies 12, 14 can be any suitable embolic protection devices configured to capture particles within a body lumen of a patient. Filter bodies 12, 14 each define an interior cavity having a plurality of openings or pores, such that when the filter body is in its deployed configuration within the vessel lumen, fluid flows through the filter body and particles of the desired size are captured inside the interior cavity of the filter body. Filter bodies 12, 14 each may comprise any material that is suitably flexible and resilient, such as a mesh, e.g., a material having openings or pores. Suitable materials include, but are not limited to, those formed from sheets, films, or sponges comprised of a polymeric or metallic substance. The material of filter bodies 12, 14 may include holes formed by mechanical means such as laser drilling and punching, or by chemical means such as the selective dissolution of one or more components. Other examples of suitable materials for filter bodies 12, 14 may also include braided, knitted, woven, or non-woven fabrics that are capable of filtering particles, such as a braided tubular fabric comprising nitinol metal. Mesh fabric of nitinol material can be heat-set to assume a desired shape upon deployment within a patient's vasculature.

In some examples, the material comprising filter bodies 12, 14 has a pore size of about 30 microns to about 500 microns, such as an average pore size of about 30 microns to about 150 microns. In some examples of system 10 configured for use for a coronary procedure, filter bodies 12, 14 may each have a pore size of approximately 50 microns, although other pore sizes may also be used with coronary procedures in other examples. In addition, in some examples of system 10 configured for use for a carotid or intracranial procedure, filter bodies 12, 14, may each have a pore size of approximately 50 microns. The variation in pore size within each of filter bodies 12, 14 may be relatively minimal.

In the example shown in in FIG. 1, filter bodies 12, 14 face the same direction, such that filter mouths 20, 22 are facing the same direction relatively to blood flow in a blood vessel when filter bodies 12, 14 are deployed in the blood vessel. For example, first filter mouth 20 and second filter mouth 22 may be distal to first filter end 24 and second filter end 28, respectively. In other examples, first filter mouth 20 and second filter mouth 22 may be proximal to first filter end 16 and second filter end 18, respectively.

A configuration in which both filter mouths are oriented substantially in the same direction may help improve the retention of particles within the filter bodies during retrieval relative to embolic protection systems that are configured such that the filter mouths face opposite directions (relative to the longitudinal axis of the elongate member), or are configured such that the filter bodies are tethered to separate wires, e.g., that branch off from a main guidewire. If the mouth of a filter body is oriented partially or entirely away from the direction of blood flow, then the blood flow may flush captured particles out of the mouth of the filter body and back into the vessel. If, however, the filter mouths are oriented in substantially the same direction (relative to a common elongated member 30), and connected to a single elongated member, as with embolic protection system 10, both filter bodies 12, 14 can be retrieved while retaining the particles captured therein. In addition, having both filter mouths oriented in substantially the same direction may permit first filter body 12 to trap particles that may become dislodged or pushed out from second filter body 14 during the retrieval of second filter body 14. In some examples, first filter body 12 may have one or more dimensions that are larger than one or more corresponding dimensions of second filter body 14, thereby enabling first filter body 12 to retain particles dislodged from second filter body 14 during retrieval, in addition to the particles trapped by first filter body 12 during deployment within a vessel.

One or more advantages also may be obtained from a configuration in which filter bodies 12, 14 remain connected to a single elongated member 30 throughout deployment, use, and retrieval of embolic protection system 10. For example, the deployment and retrieval of embolic protection system 10 may be simplified relative to configurations in which filter bodies of an embolic protection system are attached to separate wires that must be separately deployed into the vessel and retrieved using multiple catheters.

Further, retrieval of filter bodies 12, 14 from the body of the patient may be facilitated by elongated member 30, e.g., compared to embolic protection systems in which filter bodies are configured to be detached from a guidewire upon deployment into a vessel. In these systems in which filter bodies are configured to be detached from a guidewire upon deployment into a vessel, deployment and retrieval may be complicated by the use of multiple catheters, or may be complicated by a migration of a filter body from a target deployment site that cannot be easily corrected by adjustment of a position of an elongated member. Thus, the examples disclosed herein provide simplified deployment and retrieval of the embolic protection system, as well as the ability to adjust the position of the filter bodies post-deployment.

Difficulties can also arise during the deployment and retrieval of an embolic protection system including a plurality of filter devices, each having its own guide structure, e.g., a guidewire. For example, the guide structures may become tangled or otherwise engaged with one another during deployment or retrieval. In the case of retrieval, the entangling of the guide structure of a plurality of filter devices may cause one or more of the filter devices to invert or evert, thereby releasing the captured particulate debris back into the bloodstream. Thus, it may be beneficial to both the operator and the patient to provide a plurality of filter bodies 12, 14 on a single guide structure 30, thereby minimizing the likelihood of filter body entanglement, inversion, or eversion. Example embolic protection systems described herein, including system 10, comprise at least two filter bodies connected to an elongated member, and, therefore, may address the issues that may occur with some systems that have filter devices to respective guide structures.

Filter bodies 12, 14 may have any suitable shape. For example, each of first filter body 12 and second filter body 14 may comprise a relatively conical, tubular, cylindrical, hemi-spherical, hemi-ovoid, or similar shape that includes either a proximally- or distally-facing mouth opening when expanded. However, other shapes may be suitable in performing a filtering function. The configuration (e.g., shape, dimensions, and the like) of the filter bodies of the examples described herein are merely illustrative and not meant to limit the scope of the invention. In the example shown in FIG. 1, first filter body 12 and second filter body 14 have substantially the same dimensions, and both comprise a relatively conical shape, e.g., a windsock-type shape.

FIGS. 2A and 2B are side views of other examples embolic protection systems. Many of the elements of system 40 of FIG. 2A and system 60 of FIG. 2B share essentially the same characteristics with like elements in FIG. 1 and will not be described again here. However, the relative proportions of the first filter body and the second filter body of each of the embolic protection systems may vary, as depicted in FIGS. 2A and 2B and described below.

In the example of system 40 shown in FIG. 2A, first filter body 42 has first filter end 46 and defines first filter mouth 50, and second filter body 44 has second filter end 48 and defines second filter mouth 52. For example, filter bodies 42, 44 may be similar to filter bodies 12, 14, respectively, of FIG. 1, but have different relative sizes. As illustrated in FIG. 2A, second filter mouth 52 is larger than first filter mouth 50, and second filter body 44 is larger than first filter body 42. However, in other examples, second filter mouth 52 may be larger than first filter mouth 50 while first filter body 42 and second filter body 44 may be the same size, as may be the case in examples in which one or more of the filter bodies has a shape other than the cone-shape depicted in FIG. 2A. For example, one or both of first filter body 42 and second filter body 44 may comprise a tubular, cylindrical, hemi-spherical, hemi-ovoid, or similar shape. The shape of the filter bodies described herein are merely illustrative and not meant to limit the scope of the invention.

The magnitude of the difference in size between first filter mouth 50 and second filter mouth 52 may vary depending upon the magnitude of the difference in size between the vessel into which first filter body 42 is intended to be deployed and the vessel into which second filter body 44 is intended to be deployed. In addition, the sizes of first filter mouth 50 and second filter mouth 52 may vary depending upon the characteristics of the vasculature into which system 40 is to be introduced. For example, the target vasculature may comprise relatively large and differently-sized arteries, such as the brachiocephalic artery and the left common carotid artery. In this example, different, dimensions of first filter mouth 50 and second filter mouth 52 may be desirable in order for embolic protection system 40 to adequately capture particles in the two arteries. In another example, the vasculature into which system 40 is to be deployed may comprise relatively smaller and differently-sized arteries, such as a right external carotid artery and a right internal carotid artery. In this example, different, dimensions of first filter mouth 50 and second filter mouth 52 may be required. As described above with respect to FIG. 1, the maximum outer dimension of at least one of a filter's mouth and body may be sized to substantially fill the lumen of the vessel in which it is to be positioned.

In the example shown in FIG. 2B, first filter body 62 has first filter end 66 and defines first filter mouth 70, and second filter body 64 has second filter end 68 and defines second filter mouth 72. Many of the elements of system 60 of FIG. 2B share essentially the same characteristics with like elements and features in FIGS. 1 and 2A, and will not be described again here. For example, filter bodies 62, 64 may be similar to filter bodies 12, 14, respectively, of FIG. 1, but have different relative sizes. However, in contrast with the filter bodies of FIG. 2A, first filter mouth 70 is larger than second filter mouth 72, and first filter body 62 may be larger than second filter body 164.

Figure 3B:
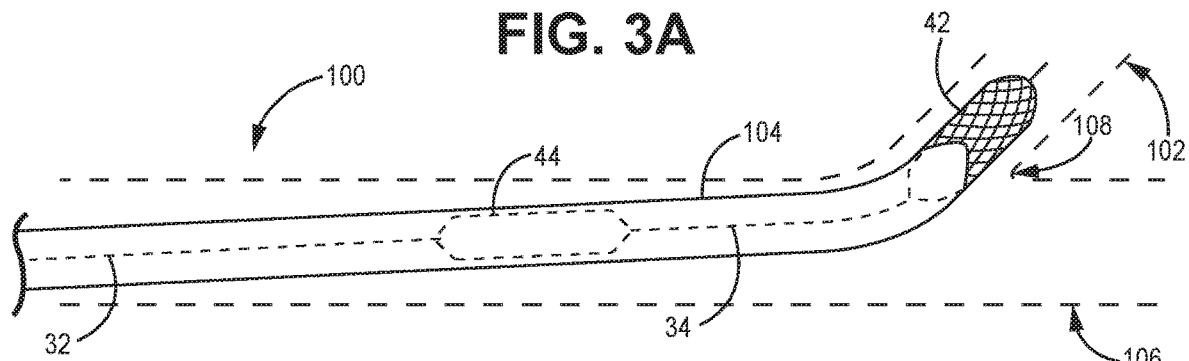
FIG. 3B is a side view of the system of FIG. 2A being introduced into a branch of the blood vessel (shown in cross-section), with the first filter body partially deployed from the delivery catheter.
Figure 3C:
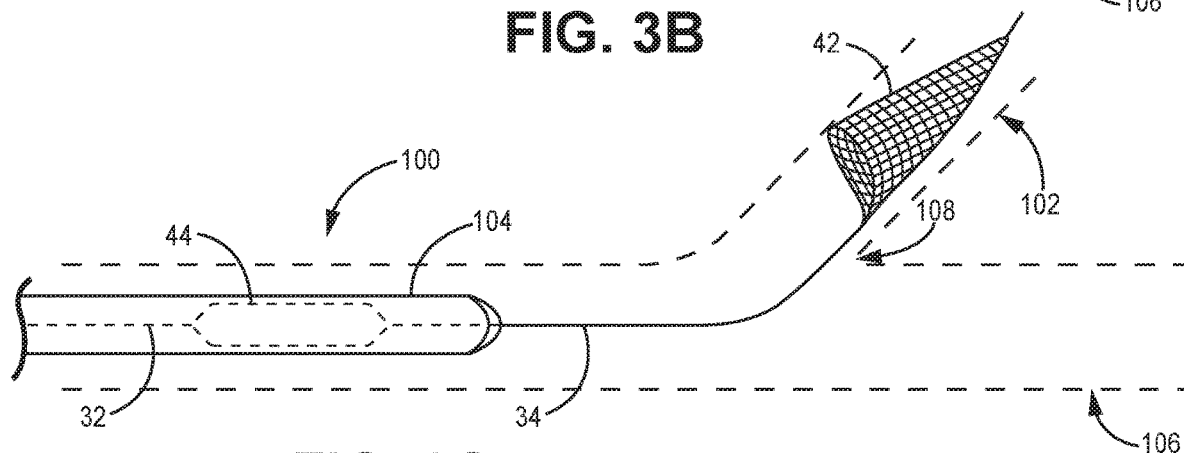
FIG. 3C is a side view of the system of FIG. 2A and illustrates the first filter body completely deployed from the delivery catheter and positioned within the branch of the blood vessel (shown in cross-section).
Figure 3D:
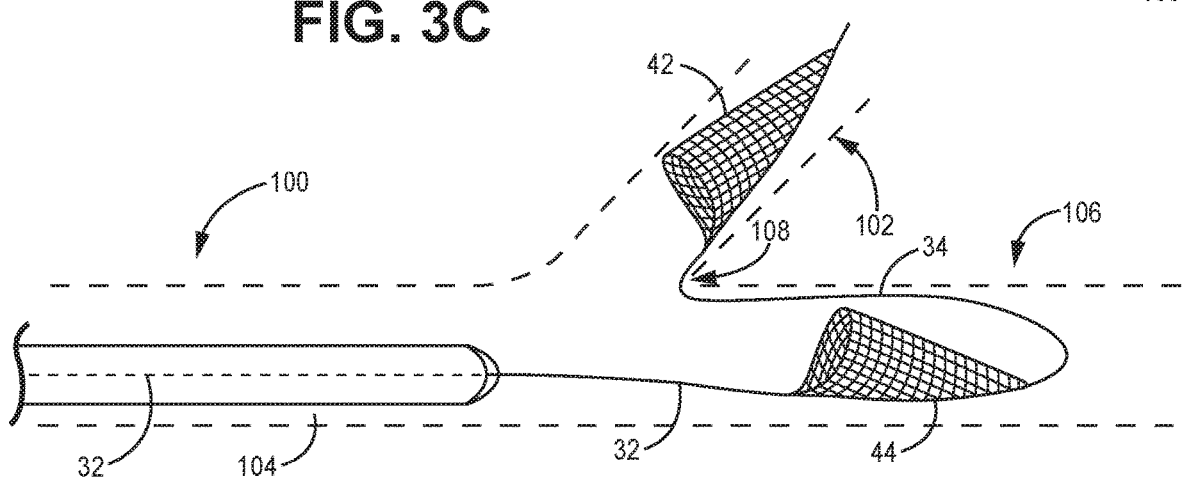
FIG. 3D is a side view of the system of FIG. 2A, and illustrates the first filter body completely deployed from the delivery catheter and positioned within the branch of the blood vessel (shown in cross-section), and the second filter body is completely deployed from the delivery catheter and positioned within the blood vessel.

FIGS. 3A-3D illustrates an example deployment of system 40 of FIG. 2A within a branched portion of the vasculature of the patient. FIGS. 3A and 3B illustrate the introduction of delivery catheter 104 through a main vessel 100 and into a first side branch 102 of main vessel 100. FIGS. 3C and 3D illustrate the deployment of first filter body 42 into first side branch 102, and the deployment of second filter body 44 into second side branch 106 of main vessel 100, respectively.

FIG. 3A illustrates system 40 of FIG. 2A being introduced into main vessel 100 (shown in cross-section) of a patient, with system 40 completely contained within delivery catheter 104. In some examples, delivery catheter 104 may comprise an elongated sheath or tube configured to be advanced through main vessel 100 to the treatment site, and having an interior lumen sized to receive system 40. In some examples, delivery catheter 104 may also be used to retrieve system 40 following the treatment procedure. In such examples, delivery catheter 104 may have an interior lumen sized to receive system 40 when filter bodies 42, 44 contain particles captured during deployment.

In FIG. 3A, filter bodies 42, 44 both are shown collapsed within the lumen of delivery catheter 104. In some examples, filter bodies 42, 44 are collapsed under the biasing force of delivery catheter 104 into a radially compressed configuration. With system 40 so contained within delivery catheter 104, delivery catheter 104 may be advanced throughout main vessel 100 to a position adjacent the treatment site, which may be downstream of an occlusion. Catheter 104 may cross the occlusion in order to reach the treatment site, or may access the treatment site downstream of the occlusion. In other examples, delivery catheter 104 may be advanced throughout main vessel 100 to a position adjacent the treatment site without system 40 contained therein, and system 40 may be subsequently delivered through delivery catheter 104.

In some examples, one or more of a guide wire and a guide catheter may first be introduced into main vessel 100 prior to the introduction of delivery catheter 104. In examples in which a guide wire is used, the guide wire may be introduced into main vessel 100 to a position adjacent to a treatment site. A position adjacent to a treatment site may be at, upstream, or downstream of an occlusion within main vessel 100. In the example of a guidewire, once the guidewire is in a position adjacent to the treatment site, delivery catheter 104 may be advanced over the guidewire, without system 40 contained therein, to the position adjacent the treatment site. The guidewire may then be withdrawn from main vessel 100, and system 40 may be advanced within delivery catheter 104 to a distal portion of delivery catheter 104.

In examples in which a guide catheter is used, the guide catheter may be introduced to the position adjacent the treatment site over a guide wire, or may be introduced on its own. Delivery catheter 104, with or without system 40 contained therein, may then be advanced within the guide catheter to the position adjacent the treatment site, and the guide catheter may then be withdrawn from main vessel 100. Once delivery catheter 104 is positioned adjacent the treatment site, system 40 may be introduced into delivery catheter 104 and traversed throughout delivery catheter 104 until reaching a position near the distal end of delivery catheter 104.

After delivery catheter 104 has been introduced into main vessel 100, as shown in FIG. 3A, a distal portion of delivery catheter 104 may be positioned within first branch 102 of main vessel 100. FIG. 3B illustrates system 40 introduced into main vessel 100 of the patient, with first filter body 42 partially deployed from a distal end of delivery catheter 104 positioned within or near first branch 102. As shown in FIG. 3B, first filter body 42 may retain a substantially compressed configuration at least until being completely deployed from delivery catheter 104. In some examples, deployment of first filter body 42 into first branch 102 may be achieved by the application of a pushing force (distally) to a proximal section 32 of elongated member 30, alone or in conjunction with the pulling back (in a proximal direction) of delivery catheter 104.

As discussed above, proximal section 32 may have sufficient stiffness be self-supporting, and to allow elongated member 30, including intermediate section 34, to be pushed distally by enough by a pushing force applied to proximal section 32 (which may be at least partially outside the body of the patient while intermediate section 34 is within the body). Thus, a clinician deploying system 40 may apply distal pushing force to a proximal section 32 of elongated member 30 without causing section 32 to kink or excessively bend. The pushing force may be translated to filter body 44, which may then be pushed against filter body 42 to cause filter body 42 to exit distally out of delivery catheter 104 and deploy into a filtering configuration within first branch 102, as shown in FIG. 3C.

In some examples, a proximal portion of filter body 42 and a distal portion (e.g., a distal tip) of filter body 44 may include complementary structures, such that filter bodies 42, 44, may mate together. For example, a proximal portion of filter body 42 may define a recess or another mating structure configured to receive a distal portion (e.g., a distal tip) of filter body 44, or the proximal portion of filter body 42 may define a projection configured to be received in a recess or another mating structure defined by a distal portion of filter body 44. The mechanical engagement between filter bodies 42, 44 provided by the complementary structures may help facilitate the translation of the pushing force from proximal section 32 to filter body 42, e.g., to move filter body 42 distally. In addition, the mechanical engagement may help keep filter bodies 42, 44 aligned during deployment, which may help reduce the time required to deploy filter bodies 42, 44.

FIG. 3C illustrates system 40 of FIG. 2A, with first filter body 42 completely deployed from delivery catheter 104 and positioned within first branch 102. As shown in FIG. 3C, first filter body 42 has assumed a radially expanded configuration such that first filter mouth 50 substantially fills the lumen of first branch 102. In this example, second filter body 44 has been advanced distally through delivery catheter 104, which has been repositioned within or near second branch 106. As illustrated in FIG. 3C, second filter body remains completely contained within delivery catheter 104 upon the deployment of first filter body 42 within first branch 102. In other examples not illustrated, second filter body 44 may be partially or completely deployed from delivery catheter 104 by the time first filter body 42 has been positioned within first branch 102.

After deploying first filter body 42 within first branch 102, as shown in FIG. 3B, second filter body 44 may be deployed into second branch 106. A distal portion of delivery catheter 104 may be repositioned within or near second side branch 106 as shown in FIG. 3C, and second filter body 44 may be deployed from delivery catheter 104 and positioned within branch 106. FIG. 3D illustrates system 40 of FIG. 2A introduced into main vessel 100 of the patient, with first filter body 42 completely deployed from delivery catheter 104 and positioned within first branch 102, and second filter body 44 completely deployed from delivery catheter 104 and positioned within second branch 106. A clinician may deploy filter 44 from delivery catheter 104 by, for example, applying a distal pushing force to a proximal section 32 of elongated member 30, and, in some examples, pulling delivery catheter 104 in a proximal direction at the same time. The pushing force may be translated to filter body 44, and cause filter body 44 to exit distally out of delivery catheter 104 and deploy into a filtering configuration within second branch 106, as shown in FIG. 3D.

In some examples, first branch 102 may be located at a portion of the vasculature distal to second branch 106. As shown in FIG. 3D, second filter body 44 has assumed a radially expanded configuration such that second filter mouth 52 substantially fills the lumen of second branch 106. Section 34 of elongated member 30 traverses arch 108 of the vasculature created by first vessel 102 and second branch 106, and is sufficiently flexible to substantially conform to the curvature of arch 108.

The length of intermediate section 34 may be selected to isolate the movement of the filter bodies 42, 44 from one another, such that movement of filter body 44 does not disrupt the positioning of filter body 42. Thus, the length of intermediate section 34 and the length between filter bodies 12, 14 may vary depending upon the characteristics (e.g., the distance between the branches 102, 106 into which the filter bodies 42, 44 are intended to be deployed, the curvature of the vasculature between the opening to branches 102, 106, and the like) of the vasculature into which system 40 is to be introduced. In the example of FIG. 3D, intermediate section 34 is preferably long enough to traverse arch 108 formed between first branch 102 and second branch 106, while simultaneously isolating movement of first filter body 42 and second filter body 44. The isolation of movement between the filter bodies may provide one or more benefits in some examples. For example, it may be desirable to deploy second filter body 44 without disrupting the position of first filter body 42 within branch 102. In addition, it may be desirable to retrieve second filter body 44 while first filter body 42 remains positioned within branch 102, thereby reducing the chance of first filter body 42 releasing particles contained therein during retrieval of second filter body 44.

As shown in FIG. 3D, a portion of proximal section 32 may remain contained within delivery catheter 104 upon full deployment of filter bodies 42, 44 at the target deployment sites. In some examples, delivery catheter 104 may then be withdrawn from main vessel 100, leaving elongated member 30 within the main vessel 100, and leaving filter bodies 42, 44 deployed within first branch 102 and second branch 106, respectively. As discussed above, in some examples, proximal section 32 of elongated member 30 is relatively stiff, e.g., and may act as a guidewire. By leaving elongated body 30 within main vessel 100, proximal section 32 may act as a guide member for guiding another device, such as a catheter for delivering a medical device (e.g., an atherectomy device, a stent, a balloon catheter, or the like), into the vasculature to the treatment site proximate filter bodies 42, 44.

In other examples, however, delivery catheter 104 may be left in main vessel 100 and may act as an outer catheter, guide catheter, or the like, for delivering another device in the patient, such as an atherectomy device, a stent, a balloon catheter, or another treatment device.

Figure 4:
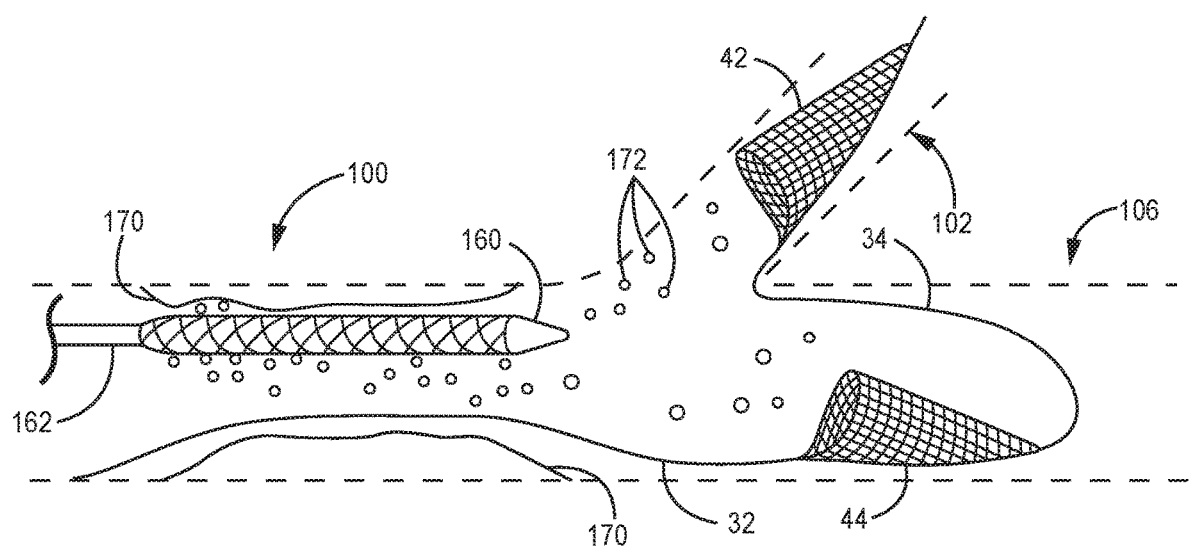
FIG. 4 illustrates the system of FIG. 2A deployed within the blood vessel (shown in cross-section) and the branch of the blood vessel, and illustrates a plaque cutting device disrupting an occlusion within the first vessel.

FIG. 4 illustrates system 40 of FIG. 2A deployed within main vessel 100 and branches 102 and 106, with treatment device 160 disrupting particles 172 from occlusion 170 within main vessel 100. Upon deployment of filter bodies 42, 44 within first branch 102 and second branch 106, respectively, treatment device 160 may be introduced into main vessel 100 and advanced to the treatment site at which occlusion 170 is located.

Treatment device 160 may be a device configured to reduce or elimination of plaque or other types of obstructions forming occlusion 170 within a vessel. For example, treatment device 160 may comprise a cutting device having one or more cutting surfaces, such as blades or burrs. In such an example, treatment device 160 may further comprise a tapered distal tip, and may be attached at its proximal end to an elongated member 162, although other configurations are contemplated. Once treatment device 160 has been positioned adjacent to occlusion 170, the cutting surfaces may be actuated and engaged with occlusion 170, thereby disrupting particles 172 from occlusion 170.

Other configurations of treatment device 160 are also within the scope of the techniques described herein. For example, treatment device 160 may alternately comprise one or more inflatable balloons, which may be configured to disrupt occlusion 170 upon inflation. In all examples, treatment of occlusion 170 with treatment device 160 may cause particles 172 to be removed from occlusion 170. Particles 172 may then be carried downstream from the treatment site within main vessel 100, into the bloodstreams of first branch 102 and second branch 106, and become captured within filter bodies 42, 44, respectively.

In some examples, one or both of first filter body and second filter body 42, 44 may become substantially filled with particles 172 prior to completion of the procedure with treatment device 160. In such examples, occlusion disruption with treatment device 160 may be suspended when filter bodies 42, 44 become substantially filled with particles 172. Filter bodies 42, 44 may then be emptied of particles 172 and re-deployed to first branch 102 and second branch 106, or a new system 40 may be introduced and new first filter body and second filter body 102, 106 deployed. Filters 42, 44 may be emptied of particles 172 using any suitable technique, such as by retrieving filter bodies 42, 44 using delivery catheter 104 or another catheter, as described below with respect to FIGS. 5A-5D, or by aspirating particles 172 from filter bodies 42, 44 using an aspiration catheter.

Following re-deployment of system 40, occlusion disruption with treatment device 160 may be resumed, and the process of removing and re-deploying system 40 may be repeated as necessary until a desired portion of occlusion 170 has been removed. In some example, substantially all of occlusion 170 may be removed. In other examples, a portion of occlusion 170 may be left in place within main vessel 100.

Figure 5A:
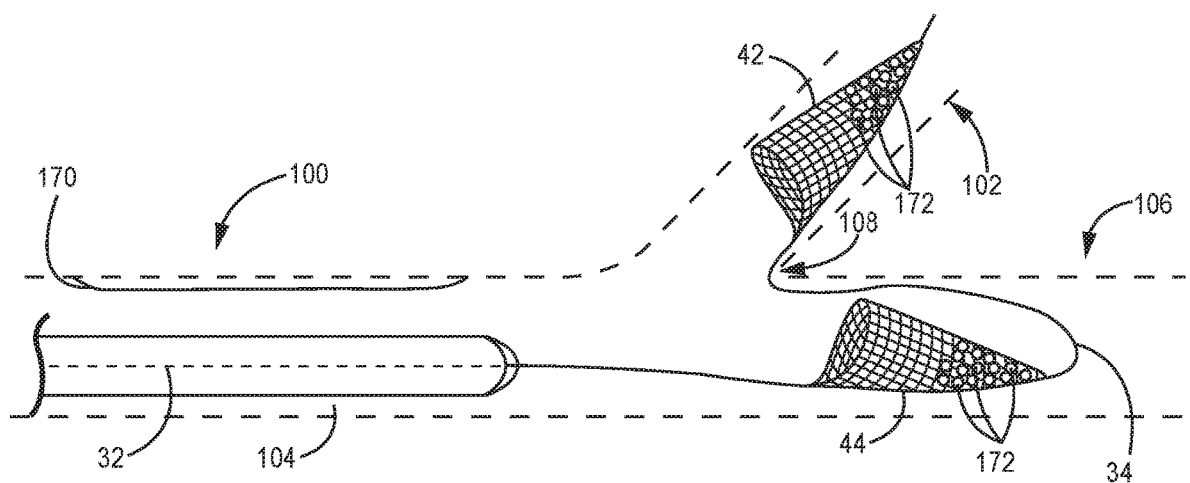
FIG. 5A illustrates the system of FIG. 2A following the disruption of the occlusion.
Figure 5B:
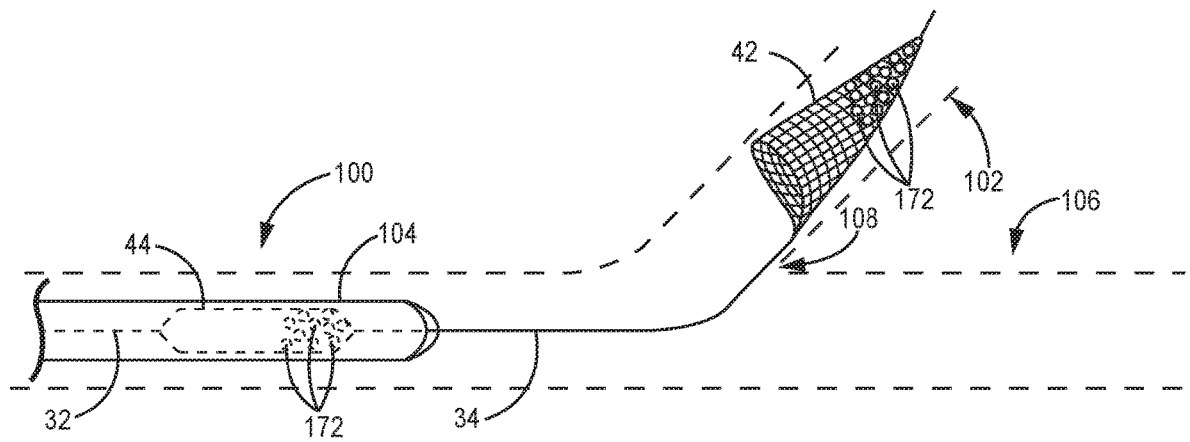
FIG. 5B illustrates the system of FIG. 2A, with the second filter body completely disposed in a catheter and the first filter body deployed in the blood vessel (shown in cross-section)
Figure 5C:
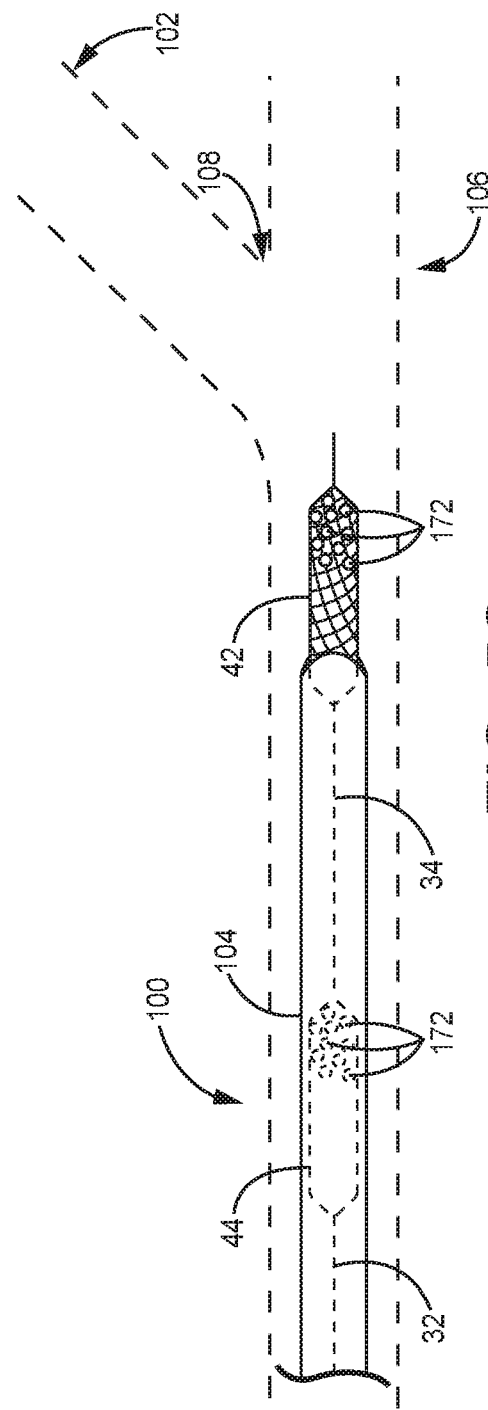
FIG. 5C illustrates the system of FIG. 2A, with the second filter body completely disposed in the catheter and the first filter body partially disposed in the catheter.
Figure 5D:
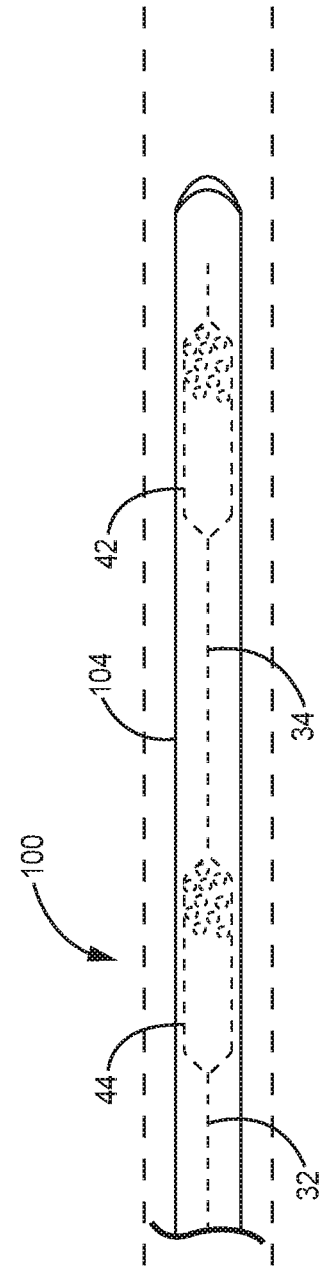
FIG. 5D illustrates the system of FIG. 2A, with both the first and second filter bodies completely disposed in the catheter.

FIGS. 5A-5D illustrates an example retrieval of system 40 of FIG. 2A from within a branched portion of the vasculature of the patient. FIG. 5A illustrates deployed filter bodies 42, 44 substantially filled with particles 172. FIG. 5B illustrates second filter body 44 being retrieved into delivery catheter 104. FIGS. 5C and 5D illustrate the retrieval of first filter body 42 into delivery catheter 104 and system 40 fully retrieved within delivery catheter 104, respectively.

FIG. 5A illustrates system 40 of FIG. 2A following the disruption of particles 172 from occlusion 170, e.g., using the occlusion disruption technique illustrated in FIG. 4 or using another suitable technique. As shown in FIG. 5A, filter bodies 42, 44 contain particles 172 removed from occlusion 170 and remain deployed within first branch 102 and second branch 106, respectively. Upon conclusion of the procedure to reduce or eliminate occlusion 170, or when filter bodies 42, 44 are relatively full and it is desirable to remove them from the patient's vasculature, treatment device 160 may be withdrawn from main vessel 100 and removed from the patient's body. In some examples, system 40 may be allowed to remain in place for a suitable length of time following the termination of the occlusion disruption (e.g., termination of the cutting of the plaque, after the inflation and subsequent deflation of a balloon, after the delivery of a stent at the occlusion 170 site, and the like) in order for particles 172 to become captured within filter bodies 42, 44. Delivery catheter 104 or another catheter (e.g., a "retrieval" catheter) may then be reintroduced to the treatment site within main vessel 100 for the retrieval of system 40. In some examples, system 40 may be withdrawn into delivery catheter 104 by a clinician holding delivery catheter 104 in place and applying a pulling force to proximal section 32 of elongated member 30. In another example, delivery catheter 104 may be advanced over system 40 by a clinician holding a proximal portion of section 32 in place and moving delivery catheter 104 distally over filter bodies 42, 44.

FIG. 5B illustrates an example of system 40 of FIG. 2A partially withdrawn into delivery catheter 104 as continued from the position of system 40 shown in FIG. 5A. Second filter body 44 is shown containing particles 172 from occlusion 170 and being completely retrieved into delivery catheter 104, whereas first filter body 42 is shown containing particles 172 from occlusion 170 and remaining deployed within first branch 102. As illustrated in FIG. 5B, second filter body 42 collapses under the biasing force of delivery catheter 104 into a radially compressed configuration upon retrieval into delivery catheter 104.

Depending upon the volume of material disrupted from occlusion 170 during the treatment procedure, the mass of particles 172 may cause the dimensions of filter bodies 42, 44 to be significantly larger upon retrieval than prior to deployment. For at least this reason, the lumen of delivery catheter 104 preferably comprises a diameter sufficient to accommodate system 40 upon retrieval. Thus, the dimensions of delivery catheter 104 may be selected based on the expected dimensions of the filter bodies upon retrieval of system 40, as well as the dimensions of the vasculature into which delivery catheter 104 is to be introduced.

FIG. 5C illustrates system 40 of FIG. 2A being withdrawn into delivery catheter 104 as continued from the position of system 40 shown in FIG. 5B. Second filter body 44 is shown containing particles 172 from occlusion 170 and completely withdrawn retrieved into delivery catheter 104. First filter body 42 is shown containing particles 172 from occlusion 170 and partially withdrawn into delivery catheter 104. As with second filter body 44, first filter body 42 collapses under the biasing force of delivery catheter 104 into a radially compressed configuration upon retrieval into delivery catheter 104. The compressed configuration of filter bodies 42, 44 upon retrieval into delivery catheter 104 may further help to minimize or even prevent particles 172 from escaping from filter bodies 42, 44 and travel back into the bloodstream of the patient.

FIG. 5D illustrates an example in which system 40 is fully into delivery catheter 104 as continued from the position of system 40 shown in FIG. 5C. Particles 172 from occlusion 170 are shown contained within filter bodies 42, 44. Delivery catheter 104 now may be withdrawn from main vessel 100 and removed from the body of the patient.

Figure 6:
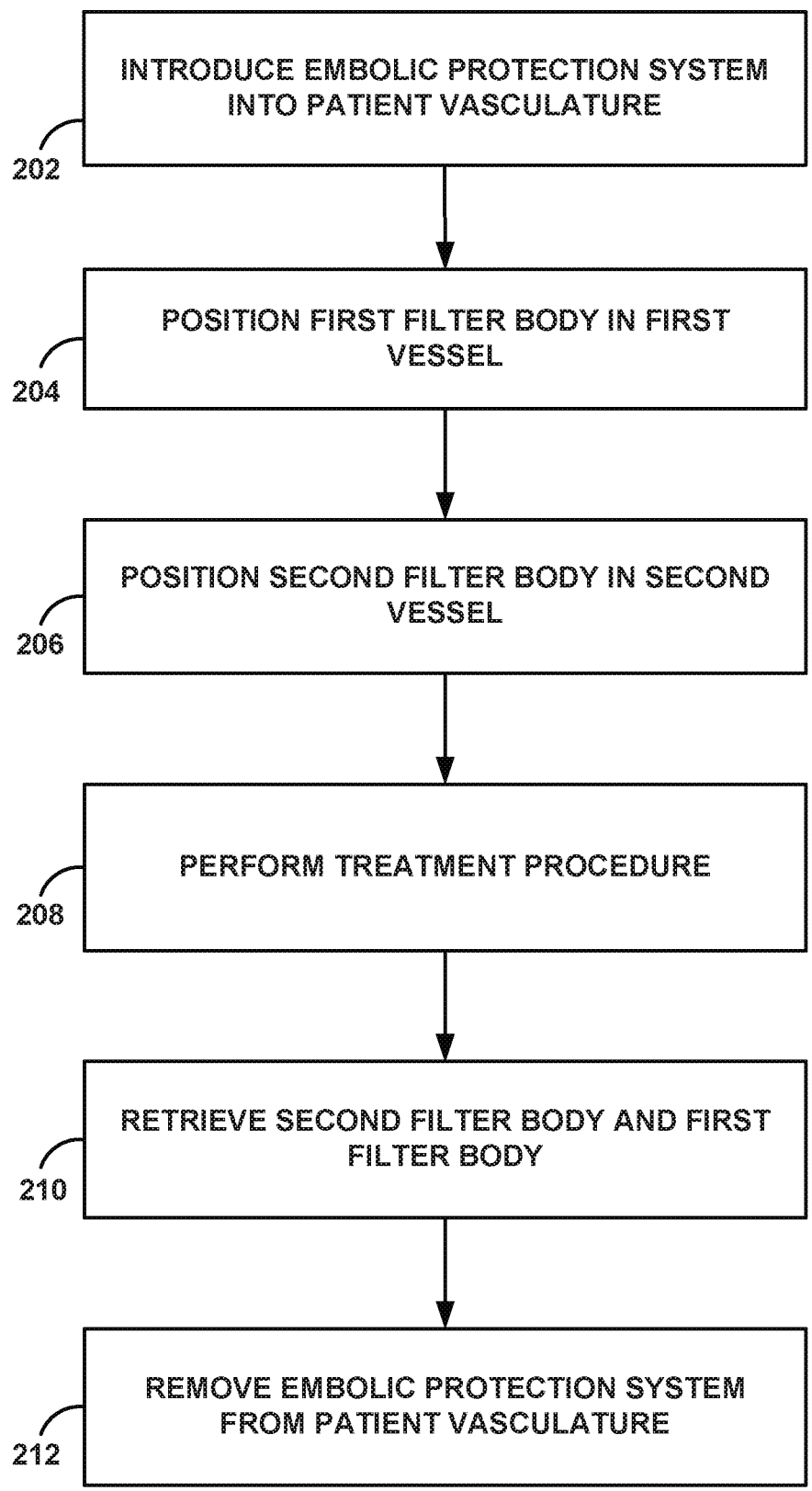
FIG. 6 is a flow diagram illustrating an example technique that may be implemented by a clinician to deploy, use, and retrieve the system of FIG. 2A.

FIG. 6 is a flow diagram illustrating example technique that may be implemented by a clinician to deploy, use, and retrieve system 40 of FIG. 2A. The technique shown in FIG. 6 is described with respect to FIGS. 2A and 3A-5D. The clinician introduces system 40 into the vasculature of a patient by any suitable means known (202). In some examples, system 40 may be introduced into the vasculature at a location relatively distant from the treatment site. The location relatively distant from the treatment site may either be upstream from the occlusion or downstream of the occlusion. Depending upon the direction from which system 40 is introduced, first filter mouth and second filter mouth 50, 52 may be configured either to both face distal section 36 of elongated member 30, or to both face proximal section 32 of elongated member 30. In some examples, system 40 may be introduced at a common femoral artery of a patient and directed to a treatment site located near a patient's heart, although numerous other vessels and treatment sites may be used. In other examples, system 40 may be introduced at a location relatively near the treatment site. In all examples, one or more components of system 40 may be sized to accommodate the dimensions of the vasculature into which system 40 is introduced, as well as the dimensions of the vasculature containing the treatment site.

Upon introduction of system 40 into the vasculature of the patient within delivery catheter 104, first filter body 42 is first positioned within first branch 102 (204), and then second filter body 44 is positioned within second branch 106 (206). Next, after filter bodies 42, 44 have been deployed at the target deployment sites, a treatment procedure may be conducted using treatment device 160, during which occlusion 170 is at least partially disrupted into particles 172 (208). Particles 172 then may be carried into first filter body 42 and second filter body 44 by the bloodstream of first branch 102 and second branch 106, respectively. Following the conclusion of the treatment procedure, or at another suitable time, second filter body 44 is withdrawn into delivery catheter 104 or another catheter, and then first filter body 42 is withdrawn into the same catheter (210). Finally, following withdrawal of system 40 into delivery catheter 104, or another catheter, the catheter is removed from the vasculature of the patient (212).

Although FIGS. 3A-6 are described with respect to embolic protection system 40 shown in FIG. 2A, in other examples, the techniques described with respect to FIGS. 3A-6 may be used with other embolic protection systems, including system 10 shown in FIG. 1 or system 60 shown in FIG. 2B, or another embolic protection system, e.g., including more than two filter bodies.

Further, although example embolic protection systems in which the filter mouths face a proximal direction, so as to capture particles in blood flowing towards a distal end of elongated member 30, in other examples, the filter bodies may face the other direction, such that the filter mouths face a distal direction. In these examples, the filter bodies may be configured to capture particles in blood flowing towards a proximal end of elongated member 30.

Various aspects of the disclosure have been described. These and other aspects are within the scope of the following claims.

What is claimed is:

1. A system comprising:
    an elongated member;
    a first filter body mechanically connected to the elongated member and defining a first filter mouth and a first filter end; and
    a second filter body mechanically connected to the elongated member distal to the first filter body, the second filter body defining a second filter mouth and a second filter end, wherein the first and second filter mouths are closer to a same end of the elongated member than the first and second filter ends, respectively, when the elongated member is in a substantially linear configuration,
    wherein at least a section of the elongated member between the first and second filter bodies is flexible and is configured to enable the first filter body to push against the second filter body when a distal pushing force is applied to a proximal section of the elongated member proximal to the first filter body, and wherein the proximal section is more stiff than the section of the elongated member between the first and second filter bodies.

2. The system of claim 1, wherein the first and second filter bodies are a same size.

3. The system of claim 1, wherein the first and second filter bodies are different sizes.

4. The system of claim 1, wherein the first filter mouth and the second filter mouth are a same size.

5. The system of claim 1, wherein the first filter mouth and the second filter mouth are different sizes.

6. The system of claim 1, wherein the first and second filter mouths are proximal to the first and second filter ends, respectively.

7. The system of claim 1, wherein the first and second filter mouths are distal to the first and second filter ends, respectively.

8. The system of claim 1, wherein the proximal section of the elongated member proximal to the first filter body is self-supporting.

9. The system of claim 1, wherein the section of the elongated member between the first and second filter bodies is configured to substantially conform to a shape of an arch between two vessels of a patient.

10. A system comprising:
an elongated member;
a first filter body mechanically connected to the elongated member and defining a first filter mouth and a first filter end; and
a second filter body mechanically connected to the elongated member distal to the first filter body, the second filter body defining a second filter mouth and a second filter end,
wherein the first filter end is between the first filter mouth and the second filter mouth when the elongated member is in a substantially linear configuration,
wherein the elongated member comprises a proximal section proximal to the first and second filter bodies and an intermediate section between the first and second filter bodies, the intermediate section being more flexible than the proximal section and configured to enable the first filter body to push against the second filter body when a distal pushing force is applied to the proximal section.

11. The system of claim 10, wherein the first and second filter bodies are a same size.

12. The system of claim 10, wherein the first and second filter bodies are different sizes.

13. The system of claim 10, wherein the first filter mouth and the second filter mouth are a same size.

14. The system of claim 10, wherein the first filter mouth and the second filter mouth are different sizes.

15. The system of claim 10, wherein the proximal section of the elongated member is self-supporting.

16. A method comprising:
introducing an embolic protection system into a vasculature of a patient, the embolic protection system comprising:
an elongated member;
a first filter body mechanically connected to the elongated member and defining a first filter mouth and a first filter end; and
a second filter body mechanically connected to the elongated member distal to the first filter body, the second filter body defining a second filter mouth and a second filter end, wherein the first and second filter mouths are closer to a same end of the elongated member than the first and second filter ends, respectively, when the elongated member is in a substantially linear configuration,
wherein at least a section of the elongated member between the first and second filter bodies is flexible and configured to enable the first filter body to push against the second filter body when a distal pushing force is applied to a proximal section of the elongated member proximal to the first filter body, and wherein the proximal section is more stiff than the section of the elongated member between the first and second filter bodies;
positioning the first filter body in a first vessel; and
positioning the second filter body in a second vessel.

17. The method of claim 16, wherein the first and second vessels are branches of a main vessel.

18. The method of claim 16, wherein introducing the embolic protection system into the vasculature of the patient comprises introducing a delivery catheter into the vasculature, the embolic protection system being positioned within an inner lumen of the delivery catheter.

19. The method of claim 16, further comprising, after positioning the first and second filter bodies in the first and second vessels, respectively, removing plaque at a treatment site in the vasculature of the patient, the first and second vessels being downstream of the treatment site.

20. The method of claim 16, further comprising, after positioning the first and second filter bodies in the first and second vessels, respectively, inflating a balloon at a treatment site in the vasculature, the first and second vessels being downstream of the treatment site.

21. The method of claim 16, further comprising, after positioning the first and second filter bodies in the first and second vessels, respectively, positioning a stent at a treatment site in the vasculature, the first and second vessels being downstream of the treatment site.

* * * * *